United States Patent [19]
Zacharia

[11] 4,079,517
[45] Mar. 21, 1978

[54] HOME PROPHYLAXIS UNIT

[75] Inventor: George Nasri Zacharia, El Cerrito, Calif.

[73] Assignee: The Denticator Company, Inc., San Francisco, Calif.

[21] Appl. No.: 720,466

[22] Filed: Sep. 3, 1976

[51] Int. Cl.² ............................................. A61C 3/06
[52] U.S. Cl. .......................................... 32/59; 15/28
[58] Field of Search ................ 32/58, 59, 27, DIG. 8; 128/62 A; 15/23, 24, 25, 26, 27, 28

[56] References Cited

U.S. PATENT DOCUMENTS

| 3,822,432 | 7/1974 | Skinner | 32/59 |
| 3,978,586 | 9/1976 | Etherington | 32/59 |

*Primary Examiner*—Robert Peshock
*Attorney, Agent, or Firm*—Townsend and Townsend

[57] ABSTRACT

A system providing a water and particle tight seal in a home prophylaxis unit is disclosed. Such units normally include a hollow plastic handle, a plastic housing extending from the handle and having a rotatable prophylaxis element at its free end, and a drive shaft within the housing which drives a prophylaxis element.

8 Claims, 4 Drawing Figures

U.S. Patent     March 21, 1978     4,079,517
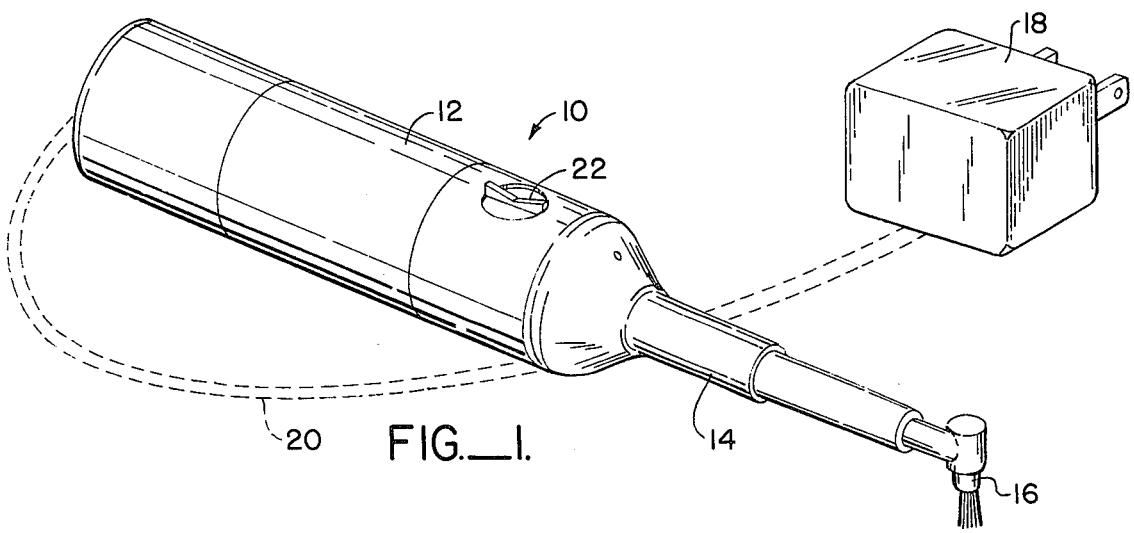
FIG._1.
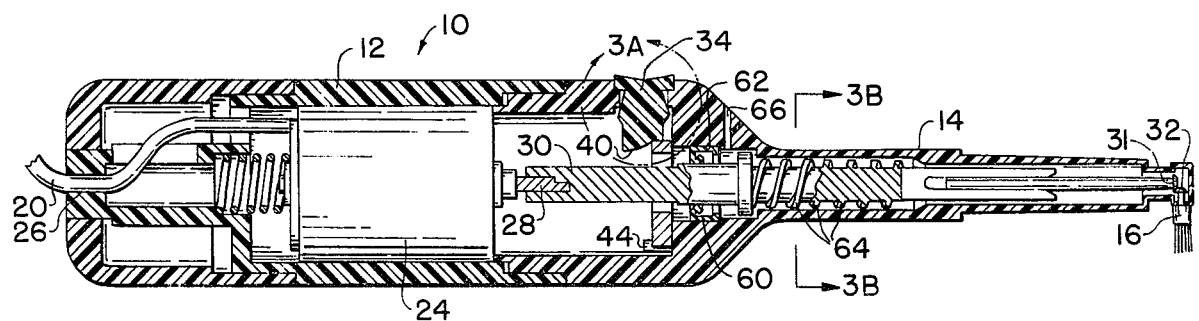
FIG._2.
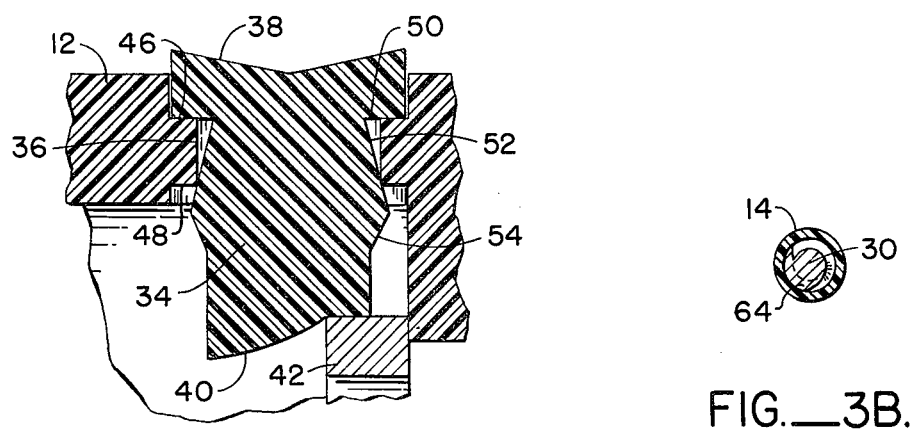
FIG._3A.
FIG._3B.

HOME PROPHYLAXIS UNIT

The system of the present invention provides a switch which includes a circular aperture counterbored at each end in the side wall of the handle, and a rotatable armature extending through the aperture. One end of the armature projects outwardly and is adapted to be rotated manually, and has an underlying lip flush with the counterbore at the exterior of the aperture. A beveled portion of the armature depends from proximate the lip and is press fit into the aperture at the counterbore at the interior of the aperture so that water tight seals are formed between the armature and the housing at both the exterior and interior of the aperture.

A non-rotatable sealing member circumscribes the shaft at a position spaced on the free end of the housing to provide a water tight seal between the housing and the drive shaft. An auger flight is attached to and circumscribes the drive shaft outboard of the sealing member to induce fluid motion toward the free end of the housing during operation of the drive shaft. In this manner, particulate matter entering the housing is forced out of the housing through the prophylaxis element and does not reach the sealing member to degrade the seal formed thereby.

BACKGROUND OF THE INVENTION

The present invention relates to home prophylaxis units, and in particular to a system for providing a water and particle tight seal to a home prophylaxis unit.

Many motorized dental instruments have been developed for home use. Such devices promote effective and efficient dental hygiene and reduce the frequency with which a dentist must be consulted. Perhaps the best known of such devices is the electric toothbrush, and water irrigation devices are also commonly used in the home. Attempts have also been made to develop a polishing instrument so that this function may be performed in the home as well. However, many difficulties have been encountered in developing such device for home use.

One of the primary concerns in developing any electric appliance for home use is proper electrical insulation so that a user will not receive an inadvertent electric shock. This is a particular problem for a home prophylaxis unit which is normally held in the user's hand and used in close proximity to water, and can in fact be accidentally immersed in water. The motor portion of the device is encased in a plastic handle, and the plastic itself is impervious to water. However, access to the interior of the handle is necessary for a switching mechanism and at the attachment of the prophylaxis element to the device. A safe and sure water tight seal must be provided at these critical points, but yet the mechanism by which the seal is effected must be reasonably inexpensive so that the devices can be offered to the consumer at reasonable costs.

SUMMARY OF THE INVENTION

The present invention provides a system for developing a water and particle tight seal in a home prophylaxis unit. Such units normally include a hollow plastic handle, a plastic shaft extending from the handle and having the rotatable prophylaxis element at its free end, and a drive shaft within the housing which drives the prophylaxis element. Water tight seals must be provided where the switch projects into the interior of the plastic handle, and between the drive shaft and the housing.

The system of the present invention provides a switch which includes a circular aperture counterbored at each end in the side wall of the handle, and a rotatable armature extending through the aperture. One end of the armature projects outwardly and is adapted to be rotated manually, and has an underlying lip flush with the counterbore at the exterior of the aperture. A beveled portion of the armature depends from proximate the lip and is press fit into the aperture so that the beveled portion extends past the counterbore at the interior of the aperture.

With the switching mechanism of the present invention, a water tight seal is formed both at the exterior and at the interior of the aperture. Because the beveled portion of the armature is press fit in the aperture, the armature is biased inwardly so that the lip remains flush with the counterbore at the exterior of the aperture to provide one sealing contact. The press fit between the bevel portion of the armature and the interior of the aperture provides a second sealing contact at the interior of the aperture. When the prophylaxis unit is constructed, the armature can be readily snapped into place in the handle, providing a quick and efficient seal for the switch at minimal construction costs.

The present invention further provides a non-rotatable sealing member which circumscribes the shaft at a position spaced from the free end of the housing to provide a water tight seal between the housing and the drive shaft. However, it has been found that a sealing member at this location is subject to deterioration by particulate matter from the prophylaxis element which passes inwardly along the interior of the housing around the drive shaft. Accordingly, the present invention also provides an auger flight which is attached to and circumscribes the drive shaft outboard of the sealing member to induce fluid motion toward the free end of the housing during operation of the drive shaft. In this manner, particulate matter entering the housing is forced out of the housing through the prophylaxis element and does not reach the sealing member to degrade the seal formed thereby.

The novel features which are characteristic of the invention, as to organization and method of operation, together with further objects and advantages thereof will be better understood from the following description considered in connection with the accompanied drawings which a preferred embodiment of the invention is illustrated by way of example. It is to be expressly understood, however, that the drawings are for the purpose of illustration and description only and are not intended as a definition of the limits of the invention.

BRIEF DESCRIPTION OF THE DRAWINGS

FIG. 1 is a perspective view of the home prophylaxis unit of the present invention;

FIG. 2 is a cross sectional elevation view of the home prophylaxis unit of FIG. 1;

FIG. 3A is an enlarged fragmentary view taken along lines 3A—3A of FIG. 2;

FIG. 3B is a cross sectional view taken along lines 3B—3B of FIG. 2.

DESCRIPTION OF THE PREFERRED EMBODIMENT

The home prophylaxis unit 10 of the present invention is illustrated generally by way of reference to FIG. 1. Unit 10 includes a hollow plastic handle 12, a shaft housing 14 emanating from the handle, and a rotatable prophylaxis element 16 at the free end of the housing. An electric motor is located within the housing 12, and is powered by means of a plug 18 inserted in a wall outlet and connected to the motor by a cord 20. A switch 22 projects to the side wall of the housing 12 to turn the electric motor on and off.

The prophylaxis unit 10 of the present invention is illustrated in more detail by way of reference to FIG. 2. Handle 12 is hollow, and contains motor 24 located therein. Cord 20 enters housing 12 through aperture 26, and since cord 20 is immovable where it enters the housing, providing a water tight seal at this juncture is not a difficult problem. The output shaft 28 of motor 24 is connected to a drive shaft 30. Drive shaft 30 extends along the interior of housing 14 and is connected to prophylaxis element 16 by means of gears 31, 32.

Motor 24 is switched on and off by means of armature 34, as illustrated in greater detail by way of reference to FIG. 3A. Armature 34 projects through an aperture 36 in the side wall of housing 12. The outer end 38 of armature 34 is manually operated to turn the armature between its "on" and "off" positions. The interior end 40 of armature 34 comprises a cam which is biased against a cam follower 42. Cam follower 42 is biased downwardly and upwardly by cam 42 when armature 34 is rotated to operate a switching element 44 which turns motor 24 on and off.

Aperture 36 has a counterbore 46 at its exterior end and a counterbore 48 at its interior end. The exterior end 38 of armature 34 has an underlying lip 50 flush with counterbore 46. Armature 34 has a beveled portion 52 depending from proximate lip 50. Armature 34 has an inwardly directed taper 54 depending from beveled portion 52 so that the armature can be forced downwardly through aperture 36 until the beveled portion is press fit against counterbore 48 on the interior of the aperture. In this position, the press fit between beveled portion 52 of armature 54 and counterbore 48 provides a water tight seal at the interior of the aperture. Furthermore, the press fit between beveled portion 52 and counterbore 48 biases armature 34 downwardly to maintain lip 50 flush with counterbore 46 to provide a water tight seal at this position also. Accordingly, the switching mechanism of the present invention provides dual water tight seals at the exterior and interior ends of aperture 36.

A sealing member 60 is located within the housing 14. Sealing member 60 is constructed of resilient material, and includes an annular lip 62 biased against shaft 30 to provide a water tight seal therebetween. However, it has been found that in use, particulate matter generated by prophylaxis element 16 enters the interior of housing 14 and passes along the shaft to sealing member 60. The particulate matter works itself between lip 62 and the shaft to degrade the water tight seal formed therebetween. In addition, much of the particulate matter is trapped by sealing member 60 and interfers with the free rotation of shaft 30 within the housing 14.

In the present invention, an auger flight 64 is mounted to and circumscribes the shaft 30 (see FIG. 3B). When drive shaft 30 is being driven by motor 24, auger flight 64 creates a fluid flow (both air and water) along the interior of housing 14 toward prophylaxis element 16. An aspiration port 66 is located between sealing member 60 and auger flight 64 to provide a supply of air to the auger flight. As a result, particulate matter entering housing 14 from prophylaxis element 16 is directed back to and through the prophylaxis element, and does not reach sealing member 60 to degrade the seal provided thereby.

It is apparent that the switching mechanism which includes armature 34 and aperture 36, sealing member 60 and auger flight 64 act in combination to provide fluid and particle tight seals for home prophylaxis unit 10. The switch is difficult to seal economically because it contains moveable parts which pass through the side wall of the housing, but these difficulties are alleviated by the switching mechanism of the present invention. Difficulties encountered in particulate matter degrading the seal between the housing and the drive shaft are alleviated by the combination of the seal of the present invention together with the auger flight discussed above. Accordingly, safe and efficient water tight seals are provided to isolate the electrical conduits of the home prophylaxis unit without infringing upon the economy of the device.

While a preferred embodiment of the present invention has been illustrated in detail, it is apparent that modifications and adaptations of that embodiment will occur to those skilled in the art. However, it is to be expressly understood that such modifications and adaptations are within the spirit and scope of the present invention, as set forth in the following claims.

What is claimed is:

1. A system for providing a water and particle tight seal to a home prophylaxis unit which includes a hollow plastic handle, a plastic shaft housing extending from said handle and having a rotatable prophylaxis element at its free end, and a drive shaft within said housing and adapted to drive said prophylaxis element, which comprises:

switch means including a circular aperture in the side wall of the hollow plastic handle counterbored at each end and a rotatable armature having one end projecting outwardly from the aperture and adapted to be rotated manually, a lip underlying said one end substantially flush with the counterbore at the exterior of the aperture, and a beveled portion depending from said one end and press fit into said aperture at the counterbore at the interior of said aperture to form a water tight seal at both the exterior and interior of said aperture;

a non-rotatable sealing member circumscribing the shaft at a position spaced from the free end of the housing to provide a water tight seal between the housing and the drive shaft; and an auger flight attached to and circumscribing the drive shaft outboard of the sealing member and adapted to induce fluid motion toward the free end of the housing during operation of said drive shaft so that particulate matter entering the housing is forced out of the housing through the prophylaxis element and does not reach the sealing member to degrade the seal formed thereby.

2. A system as recited in claim 1 wherein the rotatable armature of the switch means includes a cam at the second end opposite from said one end, said cam adapted to actuate a switching element upon rotation of the armature.

3. A system as recited in claim 1 wherein said non-rotatable sealing member includes an annular lip of resilient material biased against the drive shaft.

4. A system as recited in claim 1 and additionally comprising an aspiration port in the side wall of the housing intermediate the auger flight and the non-rotatable sealing member.

5. In a system for providing a water and particle tight seal to a home prophylaxis unit which includes a hollow plastic handle, improved switch means comprising a circular aperture in the side wall of the hollow plastic handle, counterbored at each end, and a rotatable armature having one end projecting outwardly from the aperture and adapted to be rotated manually, a lip underlying said one end substantially flush with the exterior of the handle circumscribing the exterior of the aperture, and a beveled portion depending from said one end and press fit into said aperture to form a water tight seal.

6. A system for providing a water and particle tight seal to a home prophylaxis unit which includes a hollow plastic handle, a plastic shaft housing extending from said handle and having a rotatable prophylaxis element at its free end, and a drive shaft within said housing and adapted to drive said prophylaxis element, which comprises:

a non-rotatable sealing member circumscribing the shaft at a position spaced from the free end of the housing to provide a water tight seal between the housing and the drive shaft; and an auger flight attached to and circumscribing the drive shaft outboard of the sealing members and adapted to induce fluid motion toward the free end of the housing during operation of said drive shaft so that particulate matter entering the housing is forced out of the housing through the prophylaxis element and does not reach the sealing member to degrade the seal formed thereby.

7. A system as recited in claim 6 wherein said non-rotatable sealing member includes an annular lip of resilient material biased against the drive shaft.

8. A system as recited in claim 6 and additionally comprising an aspiration port in the side wall of the housing intermediate the auger flight and the non-rotatable sealing member.

* * * * *